(12) United States Patent
Tilson et al.

(10) Patent No.: US 12,059,128 B2
(45) Date of Patent: Aug. 13, 2024

(54) DEVICE AND METHOD FOR ENHANCED VISUALIZATION OF THE SMALL INTESTINE

(71) Applicant: NEPTUNE MEDICAL INC., Burlingame, CA (US)

(72) Inventors: Alexander Q. Tilson, Burlingame, CA (US); Garrett J. Gomes, Pleasant Hill, CA (US); Stephen J. Morris, Sunnyvale, CA (US); Eugene F. Duval, Menlo Park, CA (US); Adam S. Wigginton, Sunnyvale, CA (US)

(73) Assignee: Neptune Medical Inc., Burlingame, CA (US)

( * ) Notice: Subject to any disclaimer, the term of this patent is extended or adjusted under 35 U.S.C. 154(b) by 244 days.

(21) Appl. No.: 17/057,240

(22) PCT Filed: May 31, 2019

(86) PCT No.: PCT/US2019/034881
§ 371 (c)(1),
(2) Date: Nov. 20, 2020

(87) PCT Pub. No.: WO2019/232354
PCT Pub. Date: Dec. 5, 2019

(65) Prior Publication Data
US 2021/0137366 A1    May 13, 2021

Related U.S. Application Data

(60) Provisional application No. 62/678,857, filed on May 31, 2018.

(51) Int. Cl.
*A61B 1/00* (2006.01)
*A61B 1/04* (2006.01)

(52) U.S. Cl.
CPC ...... *A61B 1/00085* (2013.01); *A61B 1/00148* (2022.02); *A61B 1/00158* (2013.01); *A61B 1/041* (2013.01)

(58) Field of Classification Search
CPC ............ A61B 1/00085; A61B 1/00148; A61B 1/00158; A61B 1/041
See application file for complete search history.

(56) References Cited

U.S. PATENT DOCUMENTS 2,268,321 A    12/1941    Flynn
2,767,705 A    10/1956    Moore
(Continued)

FOREIGN PATENT DOCUMENTS

AU    2013207571 B1    8/2013
CN    2613655 Y    4/2004
(Continued)

OTHER PUBLICATIONS

Tilson et al.; U.S. Appl. No. 17/493,785 entitled "Dynamically rigidizing composite medical structures," filed Oct. 4, 2021.
(Continued)

*Primary Examiner* — Aaron B Fairchild
(74) *Attorney, Agent, or Firm* — Shay Glenn LLP

(57) ABSTRACT

A device for distending a body lumen for enhanced visualization with a capsule endoscope includes a plurality of struts configured to extend from the capsule endoscope, a retention mechanism configured to attach the plurality of struts to the capsule endoscope, and a trigger configured to release the retention mechanism.

19 Claims, 9 Drawing Sheets

(56) References Cited

U.S. PATENT DOCUMENTS

| | | | |
|---|---|---|---|
| 3,859,986 A | 1/1975 | Okada et al. | |
| 3,998,216 A | 12/1976 | Hosono | |
| 4,066,071 A | 1/1978 | Nagel | |
| 4,141,364 A | 2/1979 | Schultze | |
| 4,151,800 A | 5/1979 | Dotts et al. | |
| 4,176,662 A | 12/1979 | Frazer | |
| 4,425,919 A | 1/1984 | Alston, Jr. | |
| 4,551,140 A | 11/1985 | Shinohara | |
| 4,690,131 A | 9/1987 | Lyddy, Jr. et al. | |
| 4,696,544 A | 9/1987 | Costella | |
| 4,717,379 A | 1/1988 | Ekholmer | |
| 4,794,412 A | 12/1988 | Casey et al. | |
| 4,794,912 A | 1/1989 | Lia | |
| 4,815,450 A | 3/1989 | Patel | |
| 4,817,613 A | 4/1989 | Jaraczewski et al. | |
| 4,893,613 A | 1/1990 | Hake | |
| 4,913,369 A | 4/1990 | Lia et al. | |
| 4,959,058 A | 9/1990 | Michelson | |
| 4,961,738 A | 10/1990 | Mackin | |
| 5,018,436 A | 5/1991 | Evangelista et al. | |
| 5,019,121 A | 5/1991 | Krauter | |
| 5,037,386 A | 8/1991 | Marcus et al. | |
| 5,105,819 A | 4/1992 | Wollschlager et al. | |
| 5,123,421 A | 6/1992 | Sinofsky | |
| 5,125,143 A | 6/1992 | Takahashi | |
| 5,174,276 A | 12/1992 | Crockard | |
| 5,188,595 A | 2/1993 | Jacobi | |
| 5,201,908 A | 4/1993 | Jones | |
| 5,251,611 A | 10/1993 | Zehel et al. | |
| 5,337,733 A | 8/1994 | Bauerfeind et al. | |
| 5,360,440 A * | 11/1994 | Andersen | A61N 1/05 607/75 |
| 5,496,292 A | 3/1996 | Burnham | |
| 5,531,685 A | 7/1996 | Hemmer et al. | |
| 5,531,719 A | 7/1996 | Takahashi | |
| 5,577,992 A | 11/1996 | Chiba et al. | |
| 5,601,588 A | 2/1997 | Tonomura et al. | |
| 5,603,991 A | 2/1997 | Kupiecki et al. | |
| 5,607,435 A | 3/1997 | Sachdeva et al. | |
| 5,624,381 A | 4/1997 | Kieturakis | |
| 5,632,734 A | 5/1997 | Galel et al. | |
| 5,662,587 A | 9/1997 | Grundfest et al. | |
| 5,662,621 A | 9/1997 | Lafontaine | |
| 5,746,692 A | 5/1998 | Bacich et al. | |
| 5,749,828 A | 5/1998 | Solomon et al. | |
| 5,759,151 A | 6/1998 | Sturges | |
| 5,779,624 A | 7/1998 | Cheng | |
| 5,782,811 A | 7/1998 | Samson et al. | |
| 5,823,961 A | 10/1998 | Fields et al. | |
| 5,882,347 A | 3/1999 | Laan et al. | |
| 5,891,112 A | 4/1999 | Samson | |
| 5,891,114 A | 4/1999 | Chin et al. | |
| 5,906,591 A | 5/1999 | Dario et al. | |
| 5,916,145 A | 6/1999 | Chu et al. | |
| 5,916,147 A | 6/1999 | Boury | |
| 5,951,539 A | 9/1999 | Nita et al. | |
| 5,976,074 A | 11/1999 | Moriyama | |
| 6,090,099 A | 7/2000 | Samson et al. | |
| 6,159,187 A | 12/2000 | Park et al. | |
| 6,162,171 A | 12/2000 | Ng et al. | |
| 6,179,776 B1 | 1/2001 | Adams et al. | |
| 6,190,357 B1 | 2/2001 | Ferrari et al. | |
| 6,217,565 B1 | 4/2001 | Cohen | |
| 6,296,644 B1 | 10/2001 | Surat et al. | |
| 6,309,346 B1 | 10/2001 | Farhadi | |
| 6,352,503 B1 | 3/2002 | Matsu et al. | |
| 6,364,878 B1 | 4/2002 | Hall | |
| 6,368,315 B1 | 4/2002 | Gillis et al. | |
| 6,468,203 B2 | 10/2002 | Belson | |
| 6,485,409 B1 | 11/2002 | Voloshin et al. | |
| 6,503,225 B1 | 1/2003 | Kirsch et al. | |
| 6,517,477 B1 | 2/2003 | Wendlandt | |
| 6,547,724 B1 | 4/2003 | Soble et al. | |
| 6,572,538 B2 | 6/2003 | Takase | |
| 6,572,590 B1 | 6/2003 | Stevens et al. | |
| 6,579,277 B1 | 6/2003 | Rabiner et al. | |
| 6,610,007 B2 | 8/2003 | Belson et al. | |
| 6,612,982 B1 | 9/2003 | Ouchi | |
| 6,616,628 B2 | 9/2003 | Hayzelden | |
| 6,620,126 B2 | 9/2003 | Unsworth et al. | |
| 6,623,424 B2 | 9/2003 | Hayakawa et al. | |
| 6,712,832 B2 | 3/2004 | Shah | |
| 6,726,677 B1 | 4/2004 | Flaherty et al. | |
| 6,730,020 B2 | 5/2004 | Peng et al. | |
| 6,780,151 B2 | 8/2004 | Grabover et al. | |
| 6,783,491 B2 | 8/2004 | Saadat et al. | |
| 6,790,173 B2 | 9/2004 | Saadat et al. | |
| 6,793,621 B2 | 9/2004 | Butler et al. | |
| 6,793,661 B2 | 9/2004 | Hamilton et al. | |
| 6,800,056 B2 | 10/2004 | Tartaglia et al. | |
| 6,869,393 B2 | 3/2005 | Butler | |
| 6,899,673 B2 | 5/2005 | Ogura et al. | |
| 6,911,004 B2 | 6/2005 | Kim et al. | |
| 6,923,754 B2 | 8/2005 | Lubock | |
| 6,960,162 B2 | 11/2005 | Saadat et al. | |
| 6,974,411 B2 | 12/2005 | Belson | |
| 6,984,203 B2 | 1/2006 | Tartaglia et al. | |
| 7,060,199 B2 | 6/2006 | Woydt et al. | |
| 7,172,552 B2 | 2/2007 | Wendlandt | |
| 7,214,230 B2 | 5/2007 | Brock et al. | |
| 7,288,101 B2 | 10/2007 | Deem et al. | |
| 7,291,127 B2 | 11/2007 | Eidenschink | |
| 7,365,509 B2 | 4/2008 | Park et al. | |
| 7,438,712 B2 | 10/2008 | Chouinard | |
| 7,511,733 B2 | 3/2009 | Takizawa et al. | |
| 7,537,562 B2 | 5/2009 | Takano | |
| 7,559,916 B2 | 7/2009 | Smith et al. | |
| 7,591,782 B2 | 9/2009 | Fujikura | |
| 7,598,652 B2 | 10/2009 | Kornbluh et al. | |
| 7,695,428 B2 | 4/2010 | Machida | |
| 7,736,323 B2 | 6/2010 | Von Weymarn-Scharti | |
| 7,749,196 B2 | 7/2010 | Osborne et al. | |
| 7,837,615 B2 | 11/2010 | Le et al. | |
| 7,850,725 B2 | 12/2010 | Vardi et al. | |
| 7,901,347 B2 | 3/2011 | Sekiguchi et al. | |
| 7,909,755 B2 | 3/2011 | Itoi | |
| 7,918,819 B2 | 4/2011 | Karmarkar et al. | |
| 7,918,845 B2 | 4/2011 | Saadat et al. | |
| 7,931,661 B2 | 4/2011 | Saadat et al. | |
| 7,935,047 B2 | 5/2011 | Yoshida et al. | |
| 7,947,000 B2 | 5/2011 | Vargas et al. | |
| 7,957,790 B2 | 6/2011 | Kleen | |
| 7,970,455 B2 | 6/2011 | Zilberstein et al. | |
| 7,988,621 B2 | 8/2011 | Smith et al. | |
| 8,047,236 B2 | 11/2011 | Perry | |
| 8,075,476 B2 | 12/2011 | Vargas | |
| 8,092,374 B2 | 1/2012 | Smith et al. | |
| 8,109,953 B1 | 2/2012 | King, III et al. | |
| 8,123,739 B2 | 2/2012 | McQueen et al. | |
| 8,125,755 B2 | 2/2012 | Garcia et al. | |
| 8,192,422 B2 | 6/2012 | Zubiate et al. | |
| 8,206,287 B2 | 6/2012 | Matsuo | |
| 8,226,548 B2 | 7/2012 | Kucklick | |
| 8,241,299 B2 | 8/2012 | Hibner | |
| 8,246,575 B2 | 8/2012 | Viola | |
| 8,257,257 B2 | 9/2012 | Takizawa et al. | |
| 8,298,161 B2 | 10/2012 | Vargas | |
| 8,313,014 B2 | 11/2012 | Bettuchi | |
| 8,361,090 B2 | 1/2013 | Belson | |
| 8,366,606 B2 | 2/2013 | Watanabe et al. | |
| 8,388,519 B2 | 3/2013 | Garcia et al. | |
| 8,439,825 B2 | 5/2013 | Sekiguchi | |
| 8,460,179 B2 | 6/2013 | Ikeda et al. | |
| 8,485,968 B2 | 7/2013 | Weimer et al. | |
| 8,496,648 B2 | 7/2013 | Rogers | |
| 8,506,479 B2 | 8/2013 | Piskun et al. | |
| 8,517,923 B2 | 8/2013 | Belson et al. | |
| 8,545,491 B2 | 10/2013 | Abboud et al. | |
| 8,550,989 B2 | 10/2013 | Dohi et al. | |
| 8,556,804 B2 | 10/2013 | Smith et al. | |
| 8,663,096 B2 | 3/2014 | Viola | |
| 8,663,196 B2 | 3/2014 | Kassab et al. | |
| 8,708,894 B2 | 4/2014 | Smith et al. | |
| 8,721,530 B2 | 5/2014 | Ohline et al. | |

(56) References Cited

U.S. PATENT DOCUMENTS

| | | |
|---|---|---|
| 8,753,312 B2 | 6/2014 | Bowe et al. |
| 8,777,844 B1 | 7/2014 | Sadanand |
| 8,920,369 B2 | 12/2014 | Salahieh et al. |
| 8,969,639 B2 | 3/2015 | Xu et al. |
| 9,011,318 B2 | 4/2015 | Choset et al. |
| 9,066,655 B2 | 6/2015 | Stefanchik et al. |
| 9,114,228 B2 | 8/2015 | Zook et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,295,511 B2 | 3/2016 | Smith et al. |
| 9,358,073 B2 | 6/2016 | Piligian et al. |
| 9,364,955 B2 | 6/2016 | Oyota et al. |
| 9,386,910 B2 | 7/2016 | West |
| 9,498,108 B1 | 11/2016 | Lombardi |
| 9,498,198 B2 | 11/2016 | Hu et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,649,473 B2 | 5/2017 | Gregorich et al. |
| 9,763,562 B2 | 9/2017 | Avitsian |
| 9,814,372 B2 | 11/2017 | Smith et al. |
| 9,913,570 B2 | 3/2018 | Kucharski et al. |
| 9,937,324 B2 | 4/2018 | Kim et al. |
| 9,993,142 B2 | 6/2018 | Salman et al. |
| 10,092,291 B2 | 10/2018 | Voegele et al. |
| 10,307,042 B2 | 6/2019 | Lombardi |
| 10,463,495 B2 | 11/2019 | Rogers et al. |
| 11,554,248 B1 | 1/2023 | Tilson et al. |
| 2001/0041881 A1 | 11/2001 | Sarge et al. |
| 2002/0107478 A1 | 8/2002 | Wendlandt |
| 2002/0161355 A1 | 10/2002 | Wollschlager |
| 2003/0023259 A1 | 1/2003 | Dubrul et al. |
| 2003/0035048 A1 | 2/2003 | Shipp |
| 2003/0083546 A1 | 5/2003 | Butler et al. |
| 2003/0122374 A1 | 7/2003 | Ouchi et al. |
| 2003/0153866 A1 | 8/2003 | Long et al. |
| 2003/0208220 A1 | 11/2003 | Worley et al. |
| 2003/0216691 A1 | 11/2003 | Jacobson |
| 2003/0225379 A1 | 12/2003 | Schaffer et al. |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1 | 9/2004 | Ewers et al. |
| 2004/0186350 A1 | 9/2004 | Brenneman et al. |
| 2004/0242958 A1 | 12/2004 | Fujikawa et al. |
| 2004/0243227 A1 | 12/2004 | Starksen et al. |
| 2004/0260236 A1 | 12/2004 | Manning et al. |
| 2005/0005363 A1 | 1/2005 | Giori et al. |
| 2005/0010237 A1 | 1/2005 | Niazi |
| 2005/0085829 A1 | 4/2005 | Kraemer et al. |
| 2005/0165275 A1 | 7/2005 | Von Felten et al. |
| 2005/0203340 A1 | 9/2005 | Butler et al. |
| 2005/0272974 A1 | 12/2005 | Iddan |
| 2005/0277966 A1 | 12/2005 | Ewers et al. |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0129130 A1 | 6/2006 | Tal et al. |
| 2006/0192465 A1 | 8/2006 | Kornbluh et al. |
| 2006/0258906 A1 | 11/2006 | Binmoeller |
| 2006/0264707 A1 | 11/2006 | Kinney |
| 2006/0264821 A1 | 11/2006 | Vo et al. |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0045504 A1 | 3/2007 | Wollschlager |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendlandt |
| 2007/0156018 A1 | 7/2007 | Krauter et al. |
| 2007/0219411 A1 | 9/2007 | Dejima et al. |
| 2007/0239252 A1 | 10/2007 | Hopkins et al. |
| 2007/0250149 A1 | 10/2007 | Oepen et al. |
| 2007/0255101 A1 | 11/2007 | Bar Or |
| 2007/0260121 A1 | 11/2007 | Bakos et al. |
| 2008/0051635 A1 | 2/2008 | Tanaka et al. |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Salahieh et al. |
| 2008/0200762 A1 | 8/2008 | Stokes et al. |
| 2008/0214893 A1 | 9/2008 | Tartaglia et al. |
| 2008/0234546 A1 | 9/2008 | Kawano et al. |
| 2008/0242928 A1 | 10/2008 | Kawano et al. |
| 2008/0249362 A1 | 10/2008 | Jiang et al. |
| 2008/0262300 A1 | 10/2008 | Ewers et al. |
| 2008/0275299 A1 | 11/2008 | Park |
| 2009/0023983 A1 | 1/2009 | Stefanchik |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0112063 A1 | 4/2009 | Bakos et al. |
| 2009/0131752 A1 | 5/2009 | Park |
| 2009/0157068 A1 | 6/2009 | Kallel et al. |
| 2009/0187163 A1 | 7/2009 | Uihlein |
| 2009/0240202 A1 | 9/2009 | Drasler et al. |
| 2009/0259200 A1 | 10/2009 | Lampropoulos et al. |
| 2009/0264704 A1 | 10/2009 | Shtul |
| 2010/0010308 A1 | 1/2010 | Braun et al. |
| 2010/0010437 A1 | 1/2010 | Miles et al. |
| 2010/0016663 A1 | 1/2010 | Maisch et al. |
| 2010/0036363 A1 | 2/2010 | Watanabe et al. |
| 2010/0069712 A1 | 3/2010 | Yamaya |
| 2010/0069716 A1 | 3/2010 | Chin et al. |
| 2010/0076451 A1 | 3/2010 | Zwolinski et al. |
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisco et al. |
| 2011/0015729 A1 | 1/2011 | Jimenez et al. |
| 2011/0023888 A1 | 2/2011 | Vazales et al. |
| 2011/0040282 A1 | 2/2011 | Uihlein |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0087070 A1 | 4/2011 | Tilson et al. |
| 2011/0237888 A1 | 9/2011 | Matsushita |
| 2011/0245611 A1 | 10/2011 | Yeh et al. |
| 2011/0282149 A1 | 11/2011 | Vargas et al. |
| 2011/0301414 A1 | 12/2011 | Hotto et al. |
| 2011/0306950 A1 | 12/2011 | Cucin |
| 2011/0319714 A1 | 12/2011 | Roelle et al. |
| 2012/0004676 A1 | 1/2012 | Vargas |
| 2012/0022329 A1 | 1/2012 | Wagh et al. |
| 2012/0041291 A1 | 2/2012 | Ferren et al. |
| 2012/0095548 A1* | 4/2012 | Gregorich ............... A61L 31/16 623/1.46 |
| 2012/0108902 A1 | 5/2012 | Frassica et al. |
| 2012/0130173 A1 | 5/2012 | Lutze et al. |
| 2012/0143005 A1 | 6/2012 | Yeh et al. |
| 2012/0165607 A1 | 6/2012 | Ashida et al. |
| 2012/0165792 A1 | 6/2012 | Ortiz et al. |
| 2012/0172651 A1 | 7/2012 | Cutrer |
| 2012/0209062 A1 | 8/2012 | Qiao |
| 2012/0277528 A1 | 11/2012 | Qiao |
| 2012/0277729 A1 | 11/2012 | Melsheimer |
| 2013/0131641 A1 | 5/2013 | Jimenez et al. |
| 2013/0190565 A1 | 7/2013 | Gora et al. |
| 2013/0338440 A1 | 12/2013 | Sinai et al. |
| 2014/0005683 A1 | 1/2014 | Stand et al. |

(56) References Cited

U.S. PATENT DOCUMENTS

| | | |
|---|---|---|
| 2014/0073853 A1 | 3/2014 | Swisher et al. |
| 2014/0081169 A1 | 3/2014 | Gerding et al. |
| 2014/0088459 A1 | 3/2014 | Roush et al. |
| 2014/0142393 A1 | 5/2014 | Piskun et al. |
| 2014/0155702 A1 | 6/2014 | Tilson et al. |
| 2014/0155783 A1 | 6/2014 | Starksen et al. |
| 2014/0188054 A1 | 7/2014 | Iijima et al. |
| 2014/0234600 A1 | 8/2014 | Wang et al. |
| 2014/0243873 A1 | 8/2014 | Franklin |
| 2014/0275860 A1 | 9/2014 | Rottenberg et al. |
| 2014/0276601 A1 | 9/2014 | Edward |
| 2014/0276642 A1 | 9/2014 | Cully et al. |
| 2014/0343358 A1 | 11/2014 | Hameed et al. |
| 2014/0371764 A1 | 12/2014 | Oyola et al. |
| 2015/0018616 A1 | 1/2015 | Kumoyama |
| 2015/0038919 A1 | 2/2015 | Bramwell et al. |
| 2015/0073216 A1 | 3/2015 | Papay |
| 2015/0073409 A1 | 3/2015 | Watson et al. |
| 2015/0094656 A1 | 4/2015 | Salahich et al. |
| 2015/0119640 A1 | 4/2015 | Reydel |
| 2015/0126814 A1 | 5/2015 | Mesallum et al. |
| 2015/0133729 A1 | 5/2015 | Reydel |
| 2015/0148602 A1 | 5/2015 | Hill et al. |
| 2015/0148606 A1 | 5/2015 | Rottenberg et al. |
| 2015/0164314 A1 | 6/2015 | Peterson |
| 2015/0216589 A1 | 8/2015 | Wittenberger et al. |
| 2015/0342608 A1 | 12/2015 | Hernandez |
| 2015/0369325 A1 | 12/2015 | Bureau et al. |
| 2016/0007832 A1 | 1/2016 | Shimada |
| 2016/0066773 A1 | 3/2016 | Cooper et al. |
| 2016/0096004 A1 | 4/2016 | Gerrans et al. |
| 2016/0129547 A1 | 5/2016 | Duescher et al. |
| 2016/0136393 A1 | 5/2016 | Tsai et al. |
| 2016/0174829 A1 | 6/2016 | Reydel |
| 2016/0198935 A1 | 7/2016 | Choi et al. |
| 2016/0270870 A1 | 9/2016 | Kowshik |
| 2016/0287059 A1 | 10/2016 | Ha et al. |
| 2016/0324412 A1 | 11/2016 | Hassidov et al. |
| 2017/0156567 A1 | 6/2017 | Kaneko |
| 2017/0157363 A1 | 6/2017 | Barrish et al. |
| 2017/0340862 A1 | 11/2017 | Calabrese et al. |
| 2017/0360281 A1 | 12/2017 | Ponsky |
| 2018/0015257 A1 | 1/2018 | Krolik et al. |
| 2018/0064366 A1 | 3/2018 | Sweeney et al. |
| 2018/0132705 A1 | 5/2018 | Higuchi |
| 2018/0184885 A1 | 7/2018 | St. George |
| 2018/0249893 A1 | 9/2018 | Yeung et al. |
| 2018/0263469 A1 | 9/2018 | Okaniwa et al. |
| 2018/0264239 A1 | 9/2018 | Piskun |
| 2018/0271354 A1 | 9/2018 | Tilson et al. |
| 2018/0289925 A1 | 10/2018 | Palmer et al. |
| 2018/0326197 A1 | 11/2018 | McArthur et al. |
| 2018/0361116 A1 | 12/2018 | Quick et al. |
| 2018/0374603 A1 | 12/2018 | Greenwood |
| 2019/0223710 A1 | 7/2019 | Tilson et al. |
| 2019/0226447 A1 | 7/2019 | Stecher et al. |
| 2020/0030575 A1 | 1/2020 | Bogusky et al. |
| 2020/0100653 A1 | 4/2020 | Nakamura |
| 2020/0171276 A1 | 6/2020 | Onozuka |
| 2020/0178763 A1 | 6/2020 | Tilson et al. |
| 2020/0315433 A1 | 10/2020 | Axon et al. |
| 2020/0383677 A1 | 12/2020 | Piligian et al. |
| 2021/0030260 A1 | 2/2021 | Julian et al. |
| 2021/0138187 A1 | 5/2021 | Tilson et al. |
| 2023/0001134 A1 | 1/2023 | Tilson et al. |
| 2023/0014281 A1 | 1/2023 | Tilson et al. |
| 2023/0120269 A1 | 4/2023 | Lopez et al. |
| 2023/0338702 A1 | 10/2023 | Tilson et al. |
| 2023/0346200 A1 | 11/2023 | Tilson et al. |
| 2023/0346204 A1 | 11/2023 | Tilson et al. |
| 2023/0346205 A1 | 11/2023 | Tilson et al. |

FOREIGN PATENT DOCUMENTS

| | | |
|---|---|---|
| CN | 1706349 A | 12/2005 |
| CN | 1732855 A | 2/2006 |
| CN | 1806770 A | 7/2006 |
| CN | 1861011 A | 11/2006 |
| CN | 101119765 A | 2/2008 |
| CN | 101129255 A | 2/2008 |
| CN | 101888872 A | 11/2010 |
| CN | 102137628 A | 7/2011 |
| CN | 201899767 U | 7/2011 |
| CN | 102711585 A | 10/2012 |
| CN | 102872519 A | 1/2013 |
| CN | 103384500 A | 11/2013 |
| CN | 104168860 A | 11/2014 |
| CN | 104287684 B | 3/2016 |
| CN | 105759418 A | 7/2016 |
| CN | 105813536 A | 7/2016 |
| CN | 105832279 A | 8/2016 |
| CN | 106137397 A | 11/2016 |
| CN | 106455929 A | 2/2017 |
| CN | 106488744 A | 3/2017 |
| CN | 106659367 A | 5/2017 |
| CN | 107296584 A | 10/2017 |
| DE | 102005039601 A1 | 2/2007 |
| EP | 401129 A1 | 12/1990 |
| EP | 0941743 A2 | 9/1999 |
| EP | 1662972 A2 | 6/2006 |
| EP | 1695657 A1 | 8/2006 |
| EP | 1487318 B1 | 3/2008 |
| EP | 2016914 A2 | 1/2009 |
| EP | 1499227 B1 | 10/2010 |
| EP | 2258322 A2 | 12/2010 |
| EP | 2364637 A1 | 9/2011 |
| EP | 2368481 A1 | 9/2011 |
| EP | 2368483 A1 | 9/2011 |
| EP | 3256052 A1 | 12/2017 |
| EP | 2604175 B1 | 11/2019 |
| GB | 2482355 A | 10/2010 |
| GB | 2497544 A | 6/2013 |
| JP | H05293077 A | 11/1993 |
| JP | 2002125921 A | 5/2002 |
| JP | 2005152300 A | 6/2005 |
| JP | 2005323778 A | 11/2005 |
| JP | 03965108 B2 | 8/2007 |
| JP | 2009507617 A | 2/2009 |
| JP | 2009061173 A | 3/2009 |
| JP | 2011194126 A | 10/2011 |
| JP | 2013176465 A | 9/2013 |
| JP | 2014124475 A | 7/2014 |
| KR | 10-2015-0131502 A | 11/2015 |
| KR | 20180053852 A | 5/2018 |
| WO | WO97/43941 A1 | 11/1997 |
| WO | WO99/053827 A1 | 10/1999 |
| WO | WO03/013348 A1 | 2/2003 |
| WO | WO2005/110199 A1 | 11/2005 |
| WO | WO2005/110200 A1 | 11/2005 |
| WO | WO2007/035931 A2 | 3/2007 |
| WO | WO2008/041809 A1 | 4/2008 |
| WO | WO2008/122969 A1 | 10/2008 |
| WO | WO2008/122997 A1 | 10/2008 |
| WO | WO2009/154192 A1 | 12/2009 |
| WO | WO2011/018147 A1 | 2/2011 |
| WO | WO2011/018157 A1 | 2/2011 |
| WO | WO2011/148172 A2 | 12/2011 |
| WO | WO2012/054480 A2 | 4/2012 |
| WO | WO2012/080947 A1 | 6/2012 |
| WO | WO2012/122288 A2 | 9/2012 |
| WO | WO2016/034598 A1 | 3/2016 |
| WO | WO2017/041052 A1 | 3/2017 |
| WO | WO2018/035452 A1 | 8/2017 |
| WO | WO2019/054867 A1 | 3/2019 |
| WO | WO2020/018934 A1 | 1/2020 |

(56) References Cited

FOREIGN PATENT DOCUMENTS

| WO | WO2020/214221 A1 | 10/2020 |
| WO | WO2020/237426 A1 | 12/2020 |

OTHER PUBLICATIONS

Tilson et al.; U.S. Appl. No. 17/448,188 entitled "Device and method for enhanced visualization of the small intestine," filed Sep. 20, 2021.
Dow. Dow white paper: Can you estimate modulus from durometer hardness for silicones: Yes, but you only roughly and you must choose your modulus carefully!; 5 pages; retrieved from the internet (https://www.dow.com/content/dam/dcc/documents/en-us/tech-art/11/11-37/11-3716-01-durometer-hardness-for-silicones.pdf) on Jan. 18, 2023.
Scheeff et al.; U.S. Appl. No. 18/000,062 entitled "Rigidizing devices," filed Nov. 28, 2022.
Gomes et al.; U.S. Appl. No. 18/044,027 entitled "Dynamically rigidizing guiderail and methods of use," filed Mar. 3, 2023.
Entrada® colonic overtube product brochure downloaded from internet http://www.usendoscopy.com/~/media/Files/Documents/Spec-Sheet-International/760358c_entrada_intl_ss_web.pdf Accessed Date: Jun. 5, 2017 (year of pub sufficiently earlier than effective US filing date and any foreign priority date) 2009.
Filip et al., Design, Implementation, and Testing of a miniature self-stabilizing capsule endoscope with wireless image transmission capabilities; Intl. Journal "information Technologies & Knowledge", 5(1): downloaded from http://www.foibg.com/ijilk/ijilx-vol05/ijitk05-1-p01.pdf on Jul. 28, 2016, (year of pub sufficiently earlier than effective US fling date and any foreign priority date) 2011.
Loeve et al.; Endoscope Shaft-Rigidity Control Mechanism: "FORGUIDE"; IEEE Trans. on Biomed. Eng.; 59(2); pp. 542-551; Feb. 2012.
Loeve et al.; Vacuum packed particles as flexible endoscope guides with controllable rigidity; Granular Matter; 12(6); pp. 543-554; Jun. 24, 2010.
Shah et al.; Magnetic Imaging of Colonoscopy: An Audit of Looping, Accuracy and Ancillary maneuvers; Gastrointest. Endosc.; 52(1); pp. 1-8; Jul. 1, 2000.
Simi et al.; Design, Fabrication, and Testing of a Capsule With Hybrid Locomotion for Gastrointestinal Tract Exploration; IEEE/ASME Trans on Mechatronics; 15(2); p. 170-x; Apr. 2010.
Valdastri et al.; Advanced Technologies for Gastrointestinal Endoscopy; Annu. Rev. Biomed. Eng.; 14; pp. 397-429; May 2012.
Zhao et al.; Development of a variable stiffness over tube based on low-melting-point-alloy for endoscopic surgery; J. Med. Devices; 10(2); 8 pages; May 12, 2016.
Bearing Works; PTFE Datasheet; 2 pages; Jan. 21, 2021 retrieved from the internet (https://www.bearingworks.com/uploaded-assets/pdfs/retainers/ptfe-datasheet.pdf) on Nov. 10, 2023.
Mayinger et al.; Disposable-sheath, flexible gastroscope system versus standard gastroscopes: a prospective, randomized trial; Gastrointestinal Endoscopy; 50(4); pp. 461-467; Oct. 1999.
Rothstein et al.; Disposable, sheathed, flexible sigmoidoscopy: a prospective, multicenter, randomized trial; Gastrointestinal Endoscopy; 41(6); pp. 566-572; Jun. 1995.
Sardinha et al.; Efficiency and productivity of a sheathed fiberoptic sigmoidoscope compared with a conventional sigmoidoscope; Diseases of the Colon and Rectum; 40(10), pp. 1248-1253; Oct. 1997.
Gomes et al.; U.S. Appl. No. 18/263,517 entitled "Devices and methods to prevent inadvertent motion of dynamically rigidizing apparatuses," filed Jul. 28, 2023.
Lopez et al.; U.S. Appl. No. 18/334,555 entitled "Layered walls for rididizing devices," filed Jun. 14, 2023.
Tilson et al.; U.S. Appl. No. 18/262,904 entitled "Large diameter hemostasis valves," filed Jul. 25, 2023.
Tilson et al.; U.S. Appl. No. 18/235,719 entitled "External working channels," filed Aug. 18, 2023.
Tanner et al.; U.S. Appl. No. 18/550,123 entitled "Control of robotic dynamically rigidizing composite medical structures," filed Sep. 11, 2023.
Tilson et al.; U.S. Appl. No. 17/604,203 entitled "Dynamically rigidizing composite medical structures," filed Oct. 15, 2021.
Tilson et al.; U.S. Appl. No. 17/644,758 entitled "Device for endoscopic advancement through the small intestine," filed Dec. 16, 2021.

\* cited by examiner

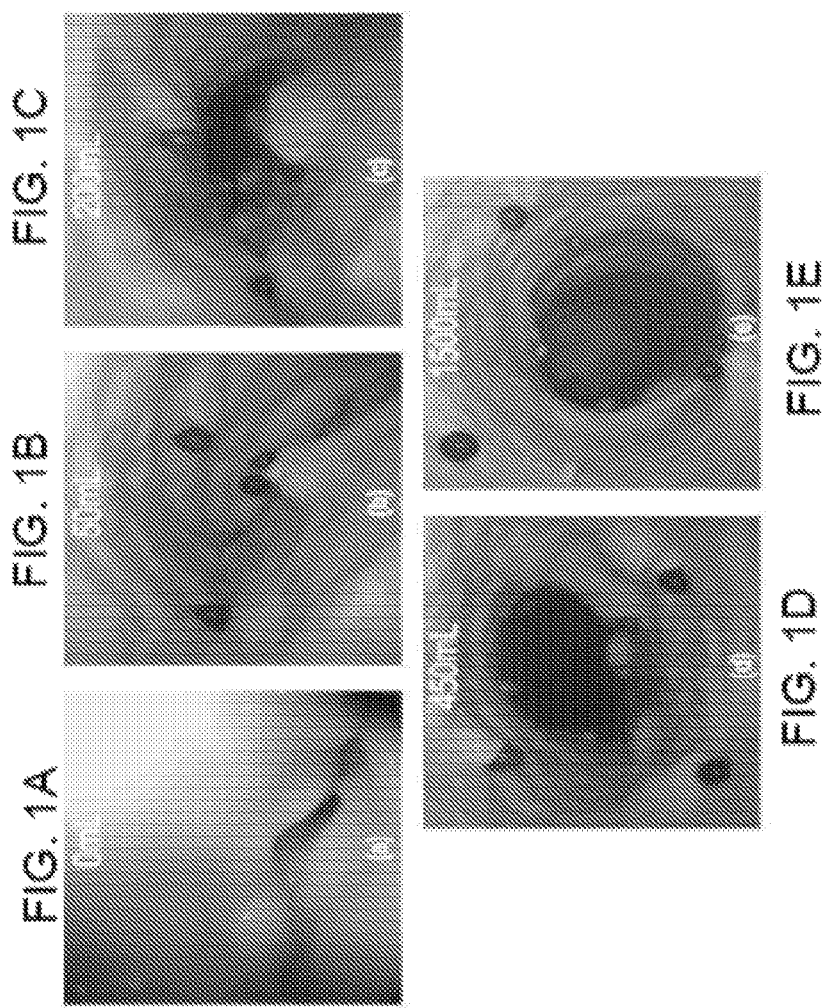

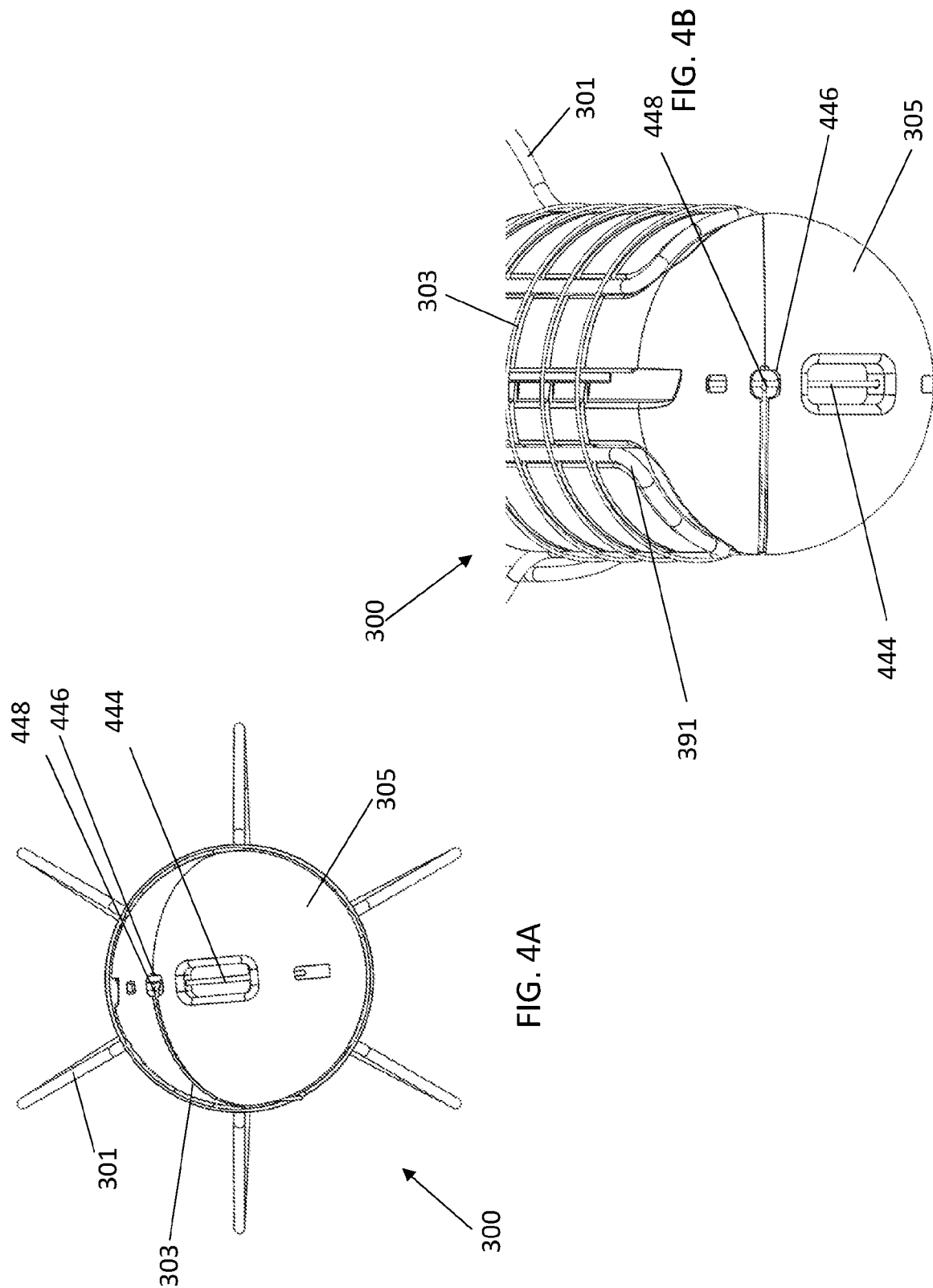

DEVICE AND METHOD FOR ENHANCED VISUALIZATION OF THE SMALL INTESTINE

CROSS REFERENCE TO RELATED APPLICATIONS

This application is a national phase application under 35 U.S.C. 371 of International Patent Application No. PCT/US2019/034881, filed on May 31, 2019, now International Publication No. WO 2019/232354, which claims priority to U.S. Provisional Patent Application No. 62/678,857, filed May 31, 2018, each of which is incorporated by reference herein.

This application may also be related to International Application No. PCT/US17/47591, filed Aug. 18, 2017, the entirety of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Endoscopy, the study or examination of the inside of the body, is a common procedure performed by gastroenterologists inside of the gastrointestinal (GI) tract. It is typically accomplished with long, slender endoscopes, either rigid or flexible.

For typical endoscopy, visualization of the GI tract is significantly enhanced by insufflation, i.e., the release of pressurized gas (air or CO2). Because collapsed tissue inhibits visualization, insufflation is used to expand or distend the GI tract so that it can be fully visualized. Without such inflation, endoscopy moves through only a portion of an often-flattened lumen, failing to image significant parts of the lumen. As a result, incomplete evaluation of the bowel is common when insufflation is not used. Luminal distention is therefore often critical for endoscopy for better visualization, detection, and the efficacy of the entire examination. FIGS. 1A-1E shows the advantages of insufflation distention during a typical endoscopy procedure. FIG. 1A shows the intestine in its deflated state with no markers visible. FIG. 1B shows that with just 50 mL of insufflation, 4 of the 9 markers become visible. FIG. 1C shows insufflation at 200 mL. FIG. 1D shows insufflation at 450 mL. FIG. 1E shows the intestine fully inflated at 1500 mL.

However, traditional endoscopy is invasive, usually requires anesthesia, and can be very difficult to move through the small intestine. Recently, there has been commercial success for a distinctly new class of devices known as capsule endoscopes (CE) (including pill cameras, pillcams, wireless capsule endoscopes, or video capsule endoscopes (VCE)). Capsule endoscopies have been revolutionary for gastroenterology, enabling diagnostic procedures that are non-invasive, do not require anesthesia, and provide visualization of anatomies that were previously poorly interrogated, including the small intestine. With capsule endoscopy, manufacturers have gone to great lengths to improve visualization, adding ever-more cameras, side-view cameras, rotating cameras, cameras with a widening field of view, or finer resolution, an increased quantity of more powerful LEDs, faster data transfer rates, and radically higher frame rates. However, none of these improvements are meaningful or helpful if the lumen is flattened and/or covers the lens.

For capsule endoscopy, luminal expansion techniques are currently not available. As such, the procedure's visualization, and thus its entire diagnostic yield and efficacy, is significantly limited. FIGS. 2A-2D show exemplary instances in which the field of view with a capsule endoscope can be obscured. FIG. 2A, for example, shows the lumen 200 collapsed around the capsule endoscope 222. FIG. 2B shows scope 222 oriented towards a fold in the wall of the lumen 200. FIG. 2C shows localized immersive mucosal contact of the lumen 200 with the scope 222. Finally, FIG. 2D shows deep folds in the lumen 200, which can hinder visualization with the scope 222. These exemplary scenarios can result in occlusion of the lens, a view of only the closed tissue, and/or an impartial view caused by blood, debris, or tissue interfering with the lens. As a result, typical capsule endoscope diagnostic efficacy rates are subpar, estimated at only around 50%. Despite patient experience advantages relative to traditional endoscopic devices, these suboptimal rates have prevented the devices from reaching their potential.

Studies have been performed with capsule endoscopes that release gas into the gastrointestinal tract for insufflation, and the results show radically improved visualization. Gas release in such studies was accomplished, for example, through the release of pressurized air or as the by-product of a chemical reaction. However, storing and methodically releasing pressurized air aboard a capsule in the gastrointestinal tract is problematic. Excessive localized gas release can cause patient discomfort. Chemical reactions struggle with heat, biocompatibility, foaming and bubbles, longevity, and adequate volume.

Capsule endoscopes including built-in radial extensions have been proposed as a means of making the device more lumen-centric to improve imaging, but these structures do not serve to adequately tent small intestine tissue, as the small intestine tissue is very thin, soft, and compliant and tends to fold over onto the lens of the scope.

A device for use with a capsule endoscope that addresses some or all of these problems is thus desired.

SUMMARY OF THE DISCLOSURE

In general, in one embodiment, a device for distending a body lumen for enhanced visualization with a capsule endoscope includes a plurality of struts configured to extend from the capsule endoscope, a retention mechanism configured to attach the plurality of struts to the capsule endoscope, and a trigger configured to release the retention mechanism.

This and any other embodiments can include one or more of the following features. The retention mechanism can be a retention strap. The retention strap can be configured to extend around proximal ends of the plurality of struts and the capsule endoscope. The capsule endoscope can include a retention strap groove, and the retention strap can be configured to sit within the retention strap groove. The retention strap can include suture, string, wire, filament or braid. The trigger can be a fuse wire. The fuse wire can be configured to corrode to release the retention mechanism. The capsule endoscope can include an aperture therein that allows fluid to pass therethrough to corrode the fuse wire. The device can further include a power supply attached to the fuse wire. The battery can be configured to accelerate corrosion of the fuse wire. The fuse wire can be a galvanic time release wire. The fuse wire can include a plated cathode and an unplated anode. The plated cathode can include silver. The fuse wire can include magnesium. The retention mechanism can be a retention strap. The fuse wire can be configured to corrode to release the retention strap. The trigger can be attached to the capsule endoscope. The plurality of struts can be configured to meet at an apex. The apex can be positioned a set axial distance away from the camera lens. The apex can include at least one pin around which the struts are wound. The device can further include a second trigger configured to release the plurality of struts from one another. The second trigger can include a corrodible element.

In general, in one embodiment, a device is configured to distend a body lumen for enhanced visualization with a capsule endoscope that includes a camera lens. The device includes a plurality of struts, a retention strap, and a fuse wire. The plurality of struts are configured to extend from the capsule endoscope and meet at an apex with the apex positioned a set axial distance away from the camera lens. The retention strap is configured to extend around the plurality of struts and the capsule endoscope to attach to the capsule endoscope. The fuse wire is configured to release the retention strap.

In general, in one embodiment, a device is configured to distend a body lumen for enhanced visualization with a capsule endoscope that includes a camera lens. The device includes a plurality of struts and a fuse wire. The plurality of struts are configured to attach to and extend from the endoscope and meet at an apex with the apex positioned a set axial distance away from the camera lens. The fuse wire is configured to release the plurality of struts from the endoscope when activated.

In general, in one embodiment, a method of enhancing visualization of a body lumen includes: positioning a device including a capsule endoscope and a plurality of struts attached thereto into a body lumen; expanding the plurality of struts of the device within the body lumen such that the plurality of struts extend away from a camera lens of the capsule endoscope and meet at an apex that is positioned a set axial distance away from the camera lens; imaging with the camera lens into the body lumen; and using a magnetic force to pull the device through a pylorus.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1E show the intestine at various stages of insufflation.

FIGS. 4A-4B show the luminal expansion device of FIG. 3 with a fuse wire.

DETAILED DESCRIPTION

Described herein are devices for use with a capsule endoscope (CE) (e.g., a pill camera, pillcam, wireless capsule endoscope, or video capsule endoscope (VCE)) that significantly aid in more complete luminal visualization during capsule endoscopy. The devices create local distension of gastrointestinal luminal tissue away from the camera, improving diagnostic yield.

Figure 2A:
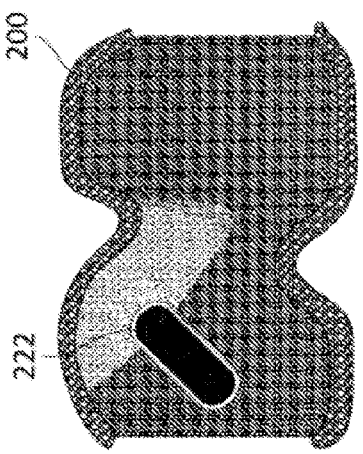
FIGS. 2A-2D are schematics showing exemplary instances in which the field of view with a capsule endoscope can be obscured.
Figure 2B:
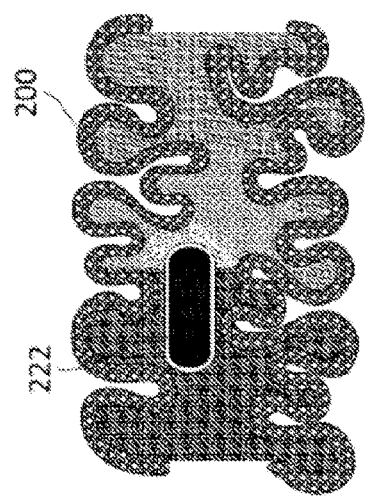
Figure 2C:
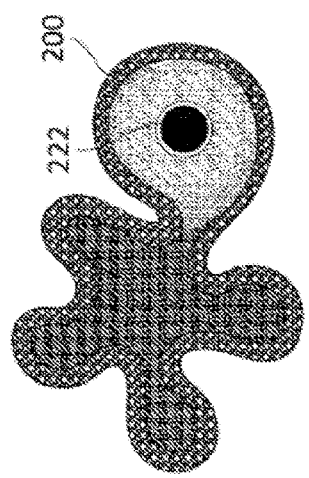
Figure 2D:
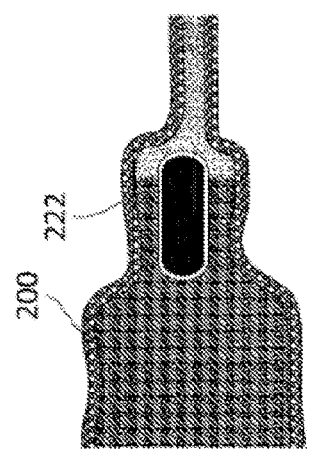
Figure 3:
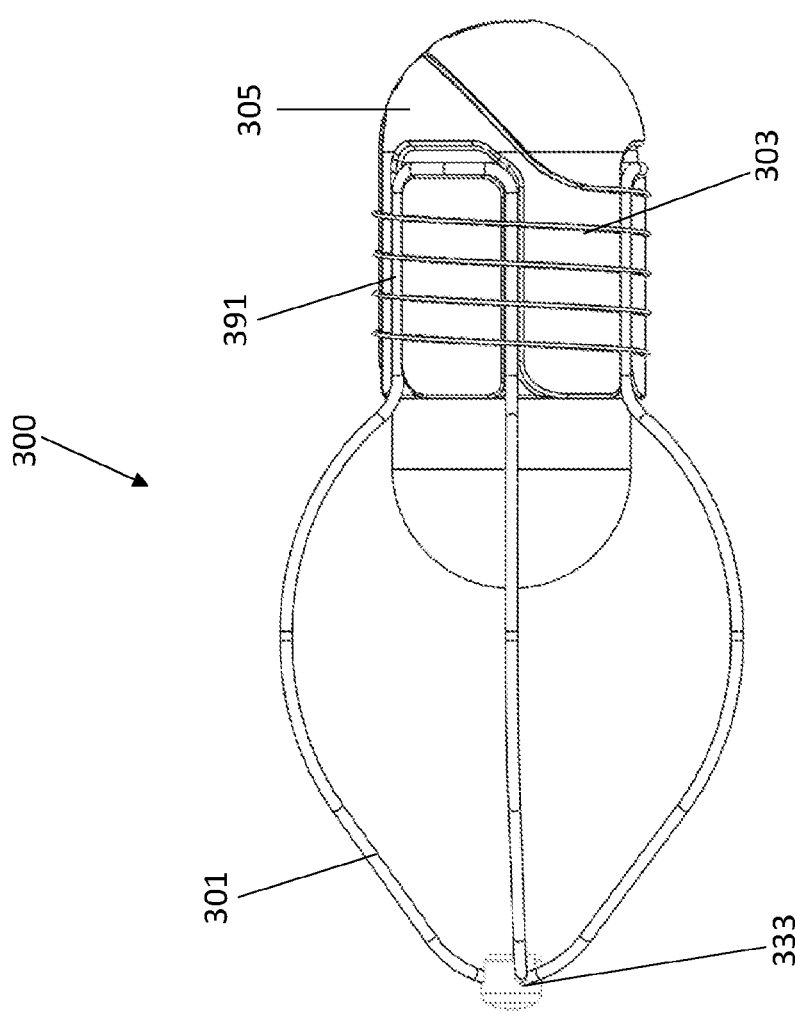
FIG. 3 shows a capsule endoscope with an exemplary luminal expansion device attached to the endoscope with a retention strap.

An exemplary luminal expansion device 300 is shown in FIG. 3. The device 300 includes a plurality of radiating struts 301 configured to attach to the capsule endoscope 305 and extend both axially and radially away from the camera lens. The struts 301 can cross or meet at an apex 333, which is positioned a maximum axial distance away from the lens of the capsule endoscope 305. Further, the struts 301 can be attached to the capsule endoscope 305 with a retention strap 303. The retention strap 303 can extend around the proximal ends 391 of the struts 301 and the central portion of the pillcam 305 to hold the struts 301 onto the pillcam 305. For example, the retention strap 303 can be wrapped a plurality of times (e.g., 2-10 times) around the proximal ends 391 and scope 305, e.g., in a spiraling fashion. The retention strap 303 can be, for example, a tensile element such as a suture, string, wire, filament, or braid.

In use, the struts 301 can be configured to distend tissue (e.g., within the small intestine) such that luminal folds are unfolded, enabling more complete visualization. The apex 333 can act as the leading edge while the wedge or conical shape of the tip can open tissue up as the device 300 moves through, maintaining an open field of view for the camera of the capsule endoscope 305. The primarily open structure of the device 300 can allow for direct, unobscured viewing of the tissue and can enable the thru-passage of matter, such as chyme, during use.

Referring to FIGS. 4A-4B, in some embodiments, the struts 301 can be released from the capsule endoscope 305 with a trigger mechanism, such as a fuse wire 444. Releasing the struts 301 from the capsule endoscope 305 can advantageously provide easier passage through the body after imaging is complete and/or release the capsule endoscope 305 if the struts 301 get caught, for example, in a polyp, stricture, or diverticulum.

The fuse wire 444 can include a section of material that is engineered to degrade with upon activation of an actuator and/or with the passage of time. For example, the fuse wire 444 can be a galvanic time release (GTR) wire. The GTR wire can include plated elements or regions (cathodes) with elements or regions of a highly active material (anode). When the GTR wire is placed in electrolyte-like gastrointestinal fluids, corrosion current between the anode and the cathode can drive electrons within the metal and ions within the electrolyte such that the active material electrochemically degrades, evolving hydrogen gas. In one example, the plating can be a silver plating either through direct deposit onto the wire or an intermediate layer, such as nickel. The silver plating can function as the cathodic portion of the wire. Alternatively, other noble metals can be used as the cathodic portion, including, for example, gold, a gold-platinum alloy, rhodium plated on silver-plated copper, silver, monel metal, or high nickel-copper alloys. The retention strap 303 can be secured around the unplated portion of the fuse wire 444. After the fuse wire 444 corrodes, the wrapped retention strap 303 can come loose and unwrap from the proximal ends 391 of the struts 301 such that the struts 301 release and become independent of the capsule endoscope 305.

In another example, the fuse wire 444 can be a nutritional metal that itself corrodes, such as magnesium. For example, the fuse wire 444 can be made of the magnesium alloy Resoloy®. As the magnesium corrodes, the magnesium can provide a portion of the recommended 420 mg per day provided by the United States Recommended Dietary Allowance. In some embodiments, part of the magnesium wire can then be plated, e.g., with silver, to act as a cathode. The amount of plating can be used to control the fuse time. For example, in some embodiments, substantially all of the wire can be plated except at the connection with the retention strap 303 so as to concentrate corrosion to a small area and minimize the fuse time. In other embodiments, a smaller length of the wire can be plated (e.g., 30-90%, such as 50-60% can be plated) so as to increase fuse time. In yet other embodiments, the plated area of the wire can be covered so as to decrease the reaction rate and increase fuse time.

In some embodiments, the fuse wire 444 can function entirely via corrosion of the materials upon use in the body (e.g., due to interaction of the fuse wire 444 with gastrointestinal fluids). In other embodiments, the fuse wire 444 can be connected to a power supply, such as a battery, to accelerate corrosion. The power supply can be activated, for example, by an external actuator, such as a magnetic actuator, or by an internal actuator in the device.

In another example, the fuse wire 444 can be made of a material that dissolves in the body (e.g., in gastrointestinal fluid), such as a polyvinyl alcohol (e.g., Vinex™ or Aquasol™) or a dissolvable suture material.

In some embodiments, the fuse wire 444 can be inserted through a bore in the capsule endoscope 305 and attached to the capsule endoscope 305 such that the remnants remain in place on the scope 305 after the selective regions of the wire 444 have corroded.

Referring to FIG. 4B, in some embodiments, there can be an aperture or open window 446 that allows gastrointestinal fluid to access the fuse wire 444. The fuse wire 444 can have a diameter, for example, of between 0.003 inches and 0.030 inches, such as around 0.015 inches.

Figure 5A:
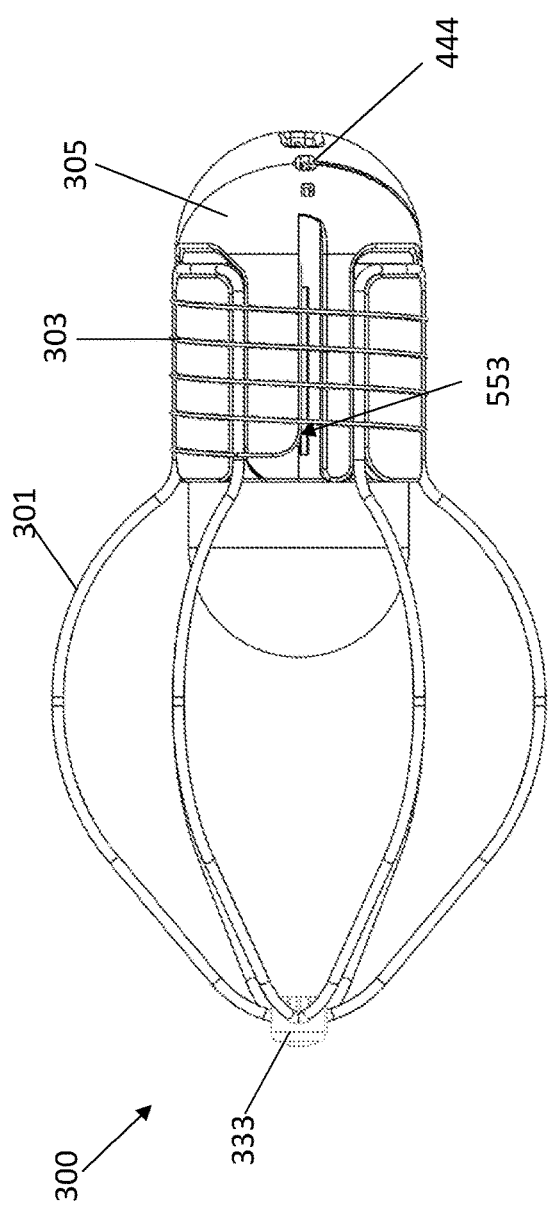
FIGS. 5A-5B show the luminal expansion device of FIG. 3 with a groove for the retention strap.
Figure 5B:
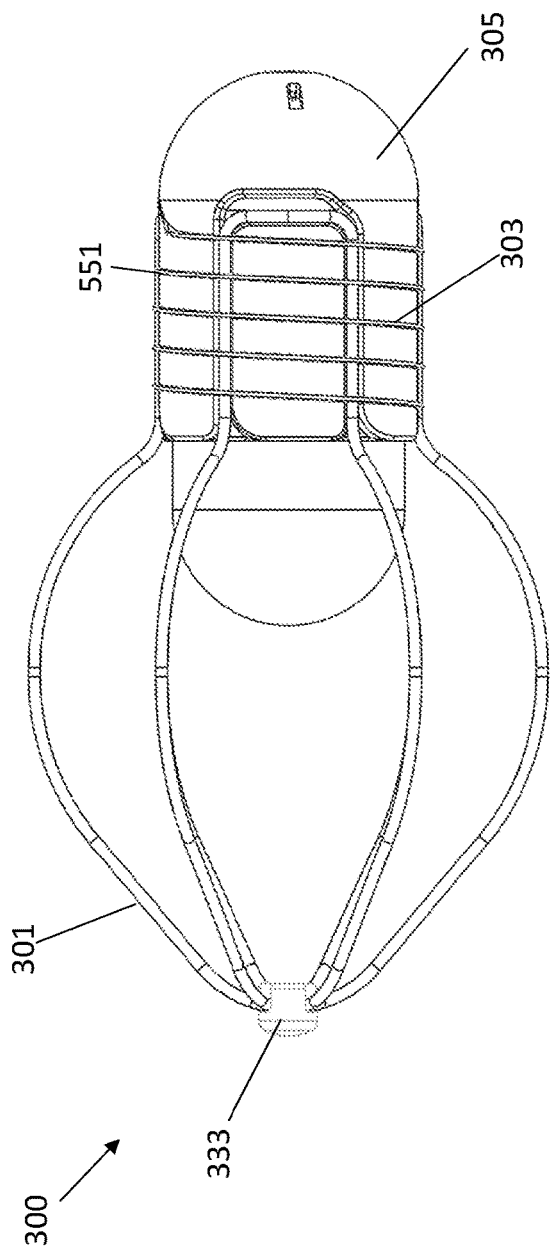

Referring to FIGS. 5A-5B, in some embodiments, the retention strap 303 can be configured to sit within one or more retention strap grooves 551 on an outer surface of the body of the capsule endoscope 305 (e.g., within a groove that spirals around the endoscope 305 a plurality of times) so as to ensure that the retention strap 303 protrudes only minimally radially outwards relative to the capsule endoscope 305 (the struts 301 can also sit within one or more grooves on the body of the endoscope 305). The retention strap 303 can further terminate in a slot 553 on the endoscope capsule 305 that allows the strap 303 to be secured thereto.

In some embodiments, to capture the struts 301 with the retention strap 303, the retention strap 303 can be tied to the fuse 444 (e.g., with a knot 448). The retention strap 303 can then be wrapped around the body of the capsule endoscope 305 and the proximal ends 391 of the struts 301. Further, in some embodiments, a pull-through loop can be used to pull the free end of the retention strap 303 back under all of the wraps of the strap 303 before terminating it in the slot 553.

In some embodiments, rather than having a separate retention strap 303 and fuse wire 444, the fuse wire itself can act as a retention member (e.g., can be configured to wrap around the proximal ends 391 of the struts 301 and the capsule endoscope 305 to hold the struts 301 onto the scope 305). In such an embodiment, the struts 301 can be released from the scope 305 upon failure of the fuse wire.

In some embodiments, the fuse or retention strap failure time can be engineered by optimizing the potential between the anode and cathode when immersed within the gastrointestinal fluid, the surface area of the fuse wire, and the cross-sectional area of the fuse wire. In some embodiments, the fuse or retention strap can be configured to fail at a longer duration than the battery of the capsule endoscope. For example, the fuse can be engineered to fail at approximately 12-15 hours. Having the fuse or retention strap fail after the battery of the capsule endoscope has been depleted can help ensure that the endoscope is safely removed after completion of imaging.

Figure 6B:
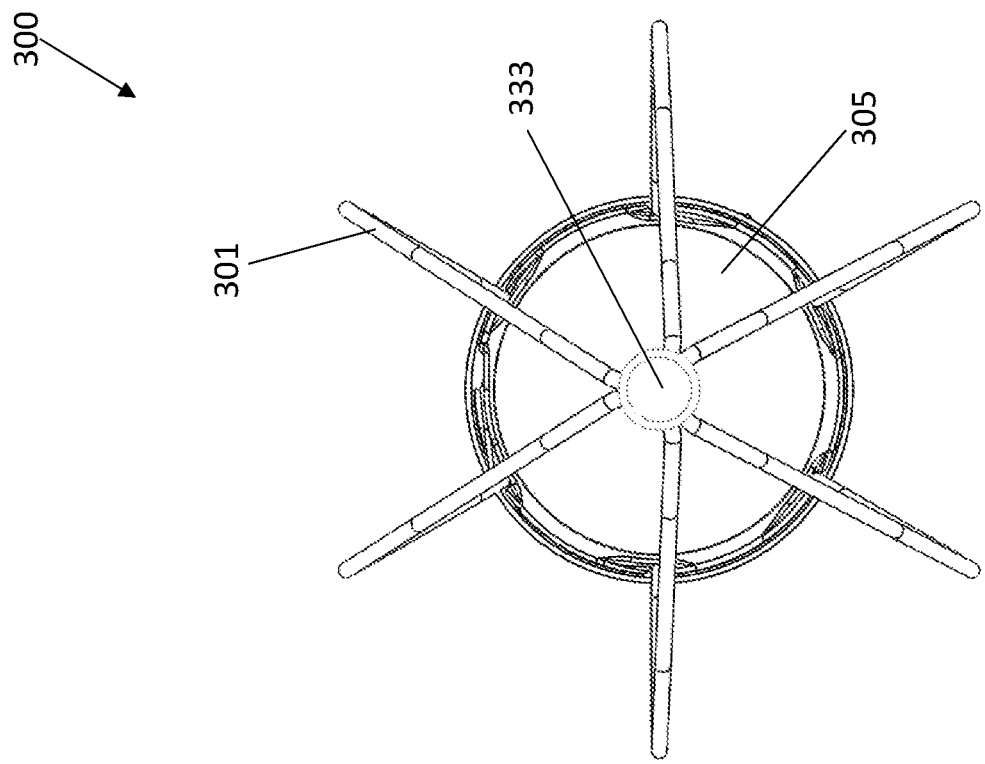
FIGS. 6A-6B show an exemplary distal apex for the luminal expansion device of FIG. 3.
Figure 6A:
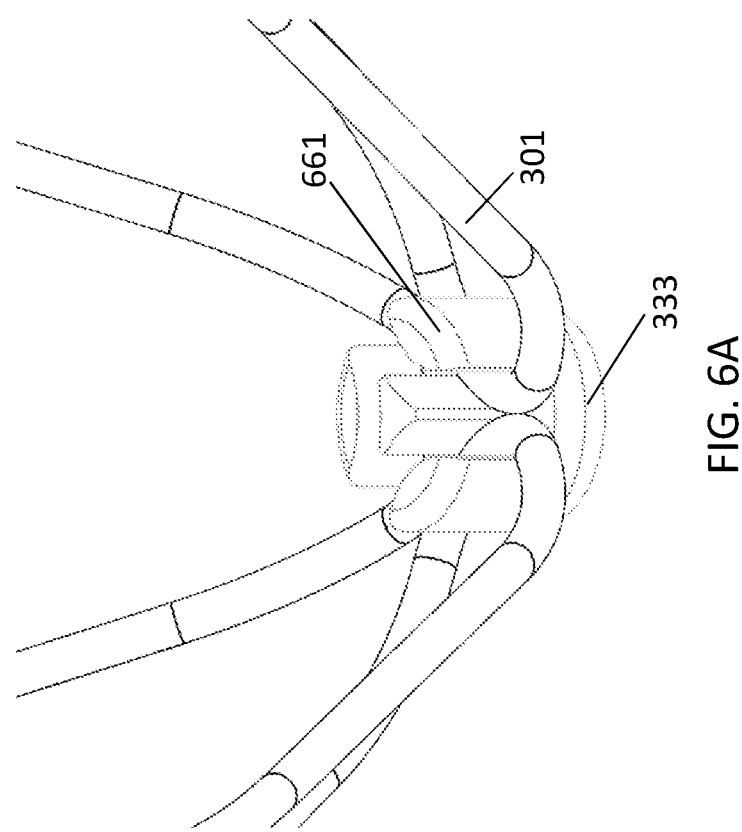

Referring to FIGS. 6A-6B, in some embodiments, the apex 333 can include a plurality of proximally extending pins 661 around which the struts 301 can wind. For example, the neighboring struts can be formed of a single elongate element that is wrapped around the pins 661. In one embodiment and as shown in FIGS. 6A-6B, there can be three pins 661, three elongate loops, and six struts 301. In another embodiment, a pin can be integrated into one of the elongate loops, and mating female hoop geometry can be integrated into the remaining two loops. Advantageously, such designs can thus allow for the struts 301 to separate at least partially from one another when the struts 301 are released from the capsule endoscope 305. In another embodiment, the apex 333 can include a separately corrodible element that releases the struts 301 from one another.

Figure 7:
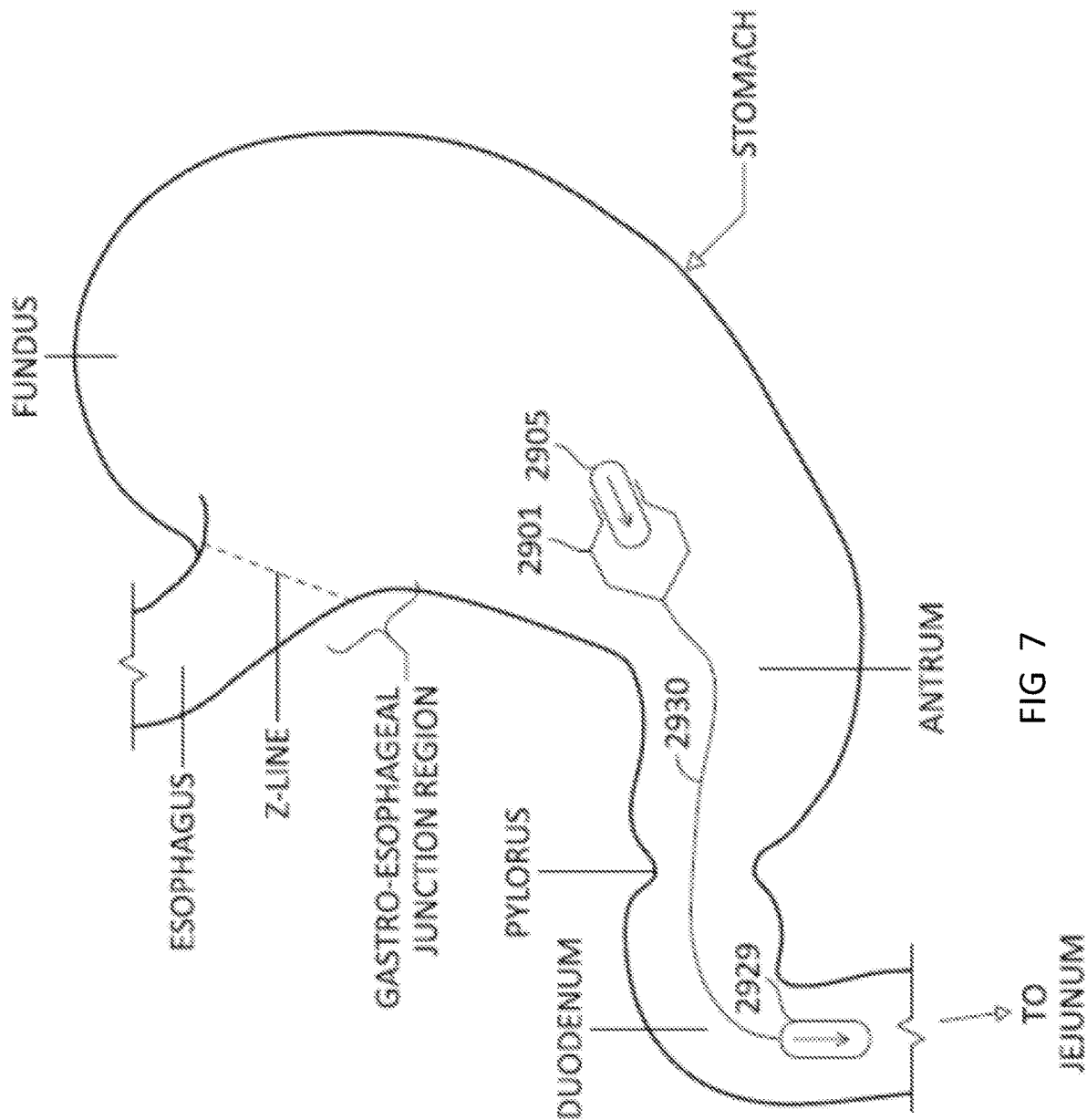
FIG. 7 shows a luminal expansion device with a tug used inside of the gastrointestinal tract.

Referring to FIG. 7, in some embodiments, a small tug element 2929 can be attached to the struts 2901 or capsule endoscope 2905 with a tensile member 2930. The small tug element 2929 can thus easily pass through the pylorus and, as it is propelled, pull the struts 2901 and attached capsule endoscope 2905 through the pylorus and into the duodenum. The tug element 2929 can, for example, be manipulated via peristalsis. Alternatively or additionally, the tug element 2929 can be manipulated by external magnetic forces that tug the device. Alternatively, the external magnetic force can act directly on a magnetic element in the luminal expansion device such that the luminal expansion device can be actively pulled through the pylorus without a tug element.

Figure 8:
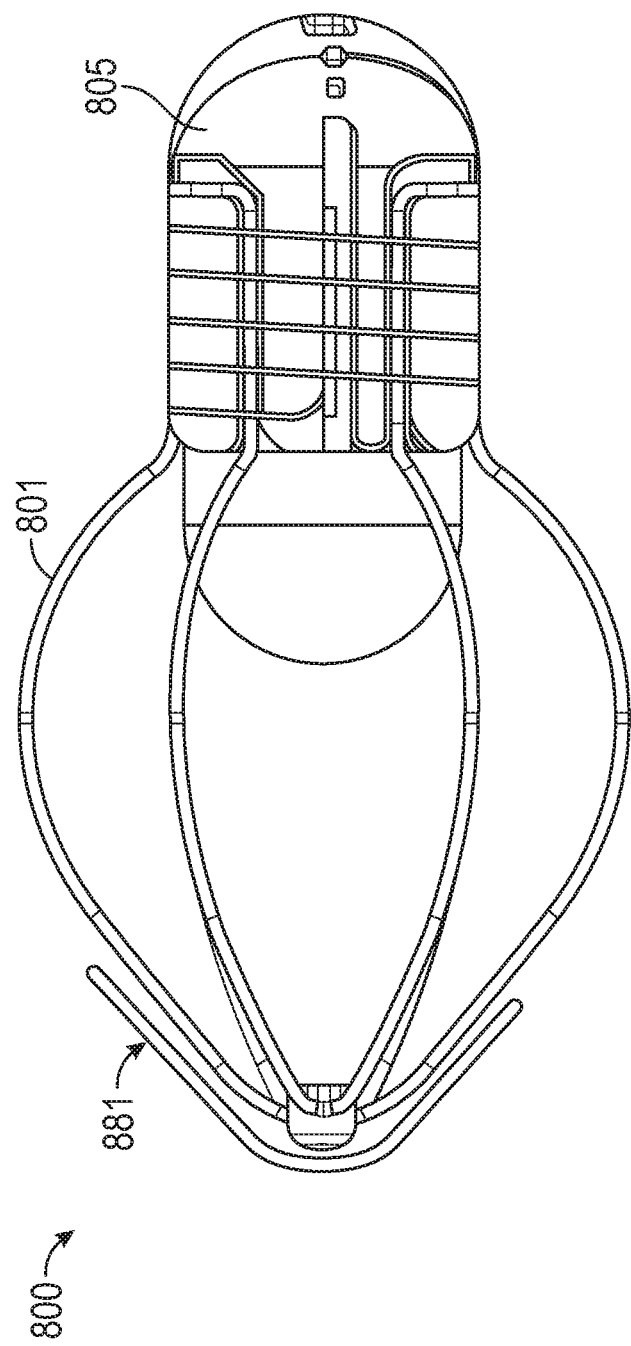
FIG. 8 shows an exemplary luminal expansion device with a lens at the distal apex.

Referring to FIG. 8, in some embodiments, a luminal expansion device 800 can include a curved lens 881 at the apex of the struts 801. The curved lens 881 can be clear (e.g., a clear plastic) to allow for imaging therethrough and can be configured to nest on top of the lens of the capsule endoscope 805 when the device 800 is in the stowed configuration. In some embodiments, the stowed configuration may comprise a gel cap that holds the expansion device 800 in a compact configuration until release (for instance, as shown in FIG. 9C). The curved lens 881 at the distal end of the device 800 can advantageously prevent wedging of the luminal expansion device into the tissue folds during use.

Figure 9A:
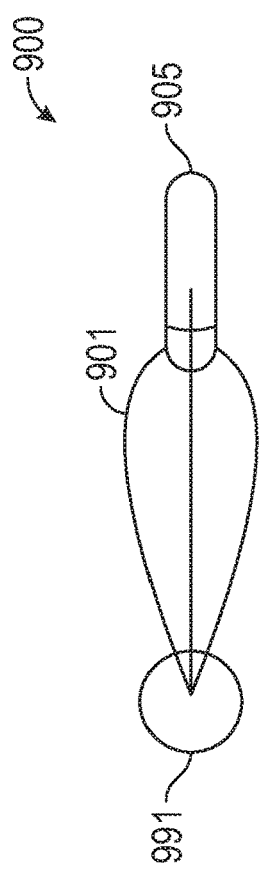
FIGS. 9A-9C show an exemplary luminal expansion device with a sphere at the distal apex.
Figure 9B:
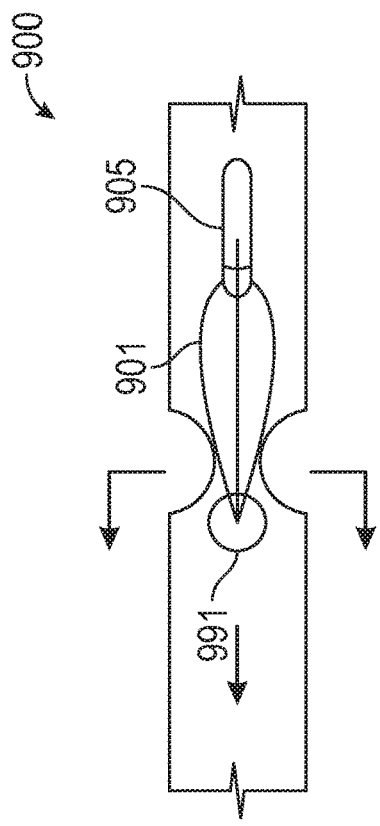
Figure 9C:
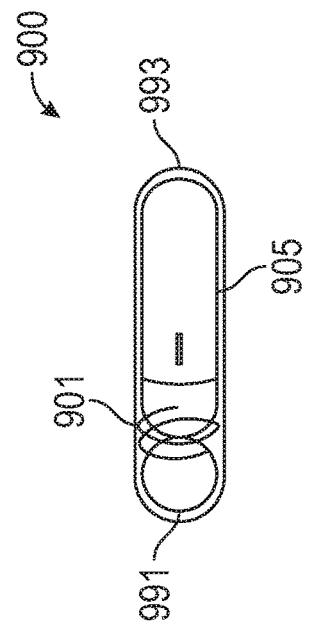

Referring to FIGS. 9A-9C, in some embodiments, a luminal expansion device 900 can include a sphere 991 at the distal apex of the struts 901. The sphere 991 can, for example, be made of a dissolvable material. Further, the sphere 991 can advantageously provide an atraumatic tip to prevent wedging of the luminal expansion device into the tissue folds during use. Additionally, as shown in FIG. 9B, the sphere 991 can assist in peristaltic movement of the device 900 and capsule endoscope 905. Similar to device

800, a dissolvable gel cap 993 can be used to hold the device 900 in the stowed configuration (see FIG. 9C).

In some embodiments, the struts of the luminal expansion devices described herein can be configured to be held in a constrained configuration by a restraining element. In some embodiments, the restraining element can be released by an external magnetic force. This can be triggered, for example, based on the location of the capsule endoscope, such as its passage through the pylorus.

Any of the features or elements of any of the expansion devices described herein may be combined or substituted for features or elements of any other expansion device.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below can be termed a second feature/element, and similarly, a second feature/element discussed below can be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A device for distending a body lumen for enhanced visualization with a capsule endoscope, the device comprising:
   a plurality of struts configured to extend from the capsule endoscope, the struts having a compact configuration having a first outmost diameter, and an expanded configuration having a second outmost diameter greater than the first outermost diameter, the struts triggerable to go from the compact configuration to the expanded configuration;
   a retention mechanism configured to attach the plurality of struts to the capsule endoscope when the plurality of struts is in an expanded configuration; and
   a trigger, comprising a fuse wire, that is configured to release the retention mechanism.

2. The device of claim 1, wherein the retention mechanism is a retention strap.

3. The device of claim 2, wherein the retention strap is configured to extend around proximal ends of the plurality of struts and the capsule endoscope.

4. The device of claim 2, wherein the capsule endoscope includes a retention strap groove, the retention strap configured to sit within the retention strap groove.

5. The device of claim 2, wherein the retention strap comprises suture, string, wire, filament or braid.

6. The device of claim 1, wherein the fuse wire is configured to corrode to release the retention mechanism.

7. The device of claim 6, wherein the capsule endoscope comprises an aperture therein that allows fluid to pass therethrough to corrode the fuse wire.

8. The device of claim 6, further comprising a power supply attached to the fuse wire, the power supply configured to accelerate corrosion of the fuse wire.

9. The device of claim 1, wherein the fuse wire is a galvanic time release wire.

10. The device of claim 1, wherein the fuse wire includes a plated cathode and an unplated anode.

11. The device of claim 10, wherein the plated cathode comprises silver.

12. The device of claim 1, wherein the fuse wire comprises magnesium.

13. The device of claim 1, wherein the retention mechanism is a retention strap, and wherein the fuse wire is configured to corrode to release the retention strap.

14. The device of claim 1, wherein the trigger is configured to be attached to the capsule endoscope.

15. The device of claim 1, wherein the plurality of struts are configured to meet at an apex.

16. The device of claim 15, wherein the apex is positioned a set axial distance away from the camera lens.

17. The device of claim 15, wherein the apex includes at least one pin around which the struts are wound.

18. The device of claim 1, further comprising a second trigger configured to release the plurality of struts from one another.

19. The device of claim 18, wherein the second trigger comprises a corrodible element.

* * * * *